United States Patent [19]

Green et al.

[11] Patent Number: 5,180,373
[45] Date of Patent: Jan. 19, 1993

[54] VALVE SYSTEM FOR INTRODUCING OBJECTS INTO ANATOMICAL BODY PORTIONS

[75] Inventors: David T. Green, Westport; Henry Bolanos, East Norwalk; Henry Sienkiewicz, Stamford, all of Conn.

[73] Assignee: United States Surgical Corporation, Norwalk, Conn.

[21] Appl. No.: 711,756
[22] Filed: Jun. 7, 1991
[51] Int. Cl.⁵ .............................................. A61M 5/00
[52] U.S. Cl. .................. 604/167; 251/149.1; 604/256
[58] Field of Search ............... 604/167, 264, 256; 251/149.1

[56] References Cited

U.S. PATENT DOCUMENTS

| | | | |
|---|---|---|---|
| 2,797,837 | 4/1954 | Roberts | 604/415 |
| 3,197,173 | 7/1965 | Taubenheim | 251/7 |
| 3,875,938 | 4/1975 | Mellor . | |
| 3,970,089 | 7/1976 | Shice | 604/256 |
| 3,977,400 | 8/1976 | Moorehead | 604/169 |
| 4,000,739 | 1/1977 | Stevens . | |
| 4,177,814 | 12/1979 | Knepshield et al. . | |
| 4,233,982 | 11/1980 | Bauer et al. . | |
| 4,240,411 | 12/1980 | Hosono . | |
| 4,243,034 | 1/1981 | Brandt | 604/169 |
| 4,338,934 | 7/1982 | Spademan . | |
| 4,379,458 | 4/1983 | Bauer et al. . | |
| 4,424,833 | 1/1984 | Spector et al. . | |
| 4,430,081 | 2/1984 | Timmermans . | |
| 4,512,766 | 4/1985 | Vailancourt . | |
| 4,531,937 | 7/1985 | Yates . | |
| 4,535,773 | 8/1985 | Yoon . | |
| 4,580,573 | 4/1986 | Quinn | 604/256 |
| 4,610,665 | 9/1986 | Matsumoto et al. . | |
| 4,610,674 | 9/1986 | Suzuki et al. . | |
| 4,611,785 | 9/1986 | Steer . | |
| 4,626,245 | 12/1986 | Weinstein . | |
| 4,629,450 | 12/1986 | Suzuki et al. . | |
| 4,634,432 | 1/1987 | Kocak . | |
| 4,654,030 | 3/1987 | Moll et al. . | |
| 4,655,752 | 4/1987 | Honkanen et al. . | |
| 4,673,393 | 6/1987 | Suzuki et al. . | |
| 4,759,751 | 7/1988 | Gabel et al. . | |
| 4,798,594 | 1/1989 | Hillstead . | |
| 4,813,938 | 3/1989 | Raulerson . | |
| 4,842,591 | 6/1989 | Luther . | |
| 4,857,062 | 8/1989 | Russell . | |
| 4,874,377 | 10/1989 | Newgard et al. . | |
| 4,895,346 | 1/1990 | Steigerwald . | |
| 4,909,798 | 3/1990 | Fleischhacker et al. . | |
| 4,917,668 | 4/1990 | Haindl . | |
| 4,929,235 | 5/1990 | Merry et al. . | |
| 4,935,010 | 6/1990 | Cox et al. . | |
| 4,960,259 | 10/1990 | Sunnanuäder et al. | 604/250 |
| 4,960,412 | 10/1990 | Fink . | |
| 4,966,588 | 10/1990 | Rayman et al. . | |
| 4,978,341 | 12/1990 | Niederhauser . | |
| 5,000,745 | 3/1991 | Guest et al. . | |
| 5,006,114 | 4/1991 | Rogers et al. . | |
| 5,009,391 | 4/1991 | Steigerwald . | |
| 5,053,014 | 10/1991 | Van Hevgten | 604/167 |
| 5,098,393 | 3/1992 | Amplatz et al. | 604/167 |
| 5,127,626 | 7/1992 | Hilal et al. | 251/149.1 |

FOREIGN PATENT DOCUMENTS

| | | |
|---|---|---|
| 29864 | 6/1981 | European Pat. Off. . |
| 054728 | 6/1982 | European Pat. Off. . |
| 344907 | 12/1989 | European Pat. Off. . |
| 350291 | 1/1990 | European Pat. Off. . |
| 2845643 | 4/1980 | Fed. Rep. of Germany . |
| 1199498 | 6/1970 | United Kingdom . |
| 2019219 | 10/1979 | United Kingdom . |
| 2063679 | 6/1981 | United Kingdom . |

Primary Examiner—Paul J. Hirsch
Attorney, Agent, or Firm—Thomas R. Bremer; Peter G. Dilworth; Rocco S. Barrese

[57] ABSTRACT

A valve assembly adapted for introduction of an elongated object into a patient's body having a first valve formed of a resilient material and defining an aperture for reception of the object, the aperture being configured and dimensioned such that insertion of the object into the aperture will cause the resilient material defining the aperture to resiliently engage the outer surface of the object in a fluid tight manner. A second valve is positioned adjacent and distal of the first valve in general alignment therewith, whereby the second valve defines an aperture in general alignment with the aperture of the first valve, and is formed of a flexible material at least in the region defining the apeture. A pair of manually operable clamps are provided to selectively permit the aperture of the second valve to be opened or closed so as to permit entry of the object such that the object first passes through the first valve and then the second valve prior to entry into the patient's body.

32 Claims, 4 Drawing Sheets

VALVE SYSTEM FOR INTRODUCING OBJECTS INTO ANATOMICAL BODY PORTIONS

BACKGROUND OF THE INVENTION

1. Field of the Invention

This invention relates to valve systems of the type adapted to allow the introduction of a surgical instrument into a patient's body. In particular, the invention is applicable to a cannula assembly and the like wherein a cannula extends from a valve assembly and is intended for insertion into a patient's body and an instrument is inserted into the patient's body through the cannula.

2. Background Of The Prior Art

In laparoscopic procedures surgery is performed in the interior of the abdomen through a small incision; in endoscopic procedures surgery is performed in any hollow viscus of the body through narrow endoscopic tubes or cannula inserted through a small entrance incision in the skin. Laparoscopic and endoscopic procedures generally require that any instrumentation inserted into the body be sealed, i.e. provisions must be made to ensure that gases do not enter or exit the body through the laparoscopic or endoscopic incision as, for example, in surgical procedures in which the surgical region is insufflated. Moreover, laparoscopic and endoscopic procedures often require the surgeon to act on organs, tissues, and vessels far removed from the incision, thereby requiring that any instruments used in such procedures be relatively long and narrow.

For such procedures, the introduction of a tube into certain anatomical cavities such as the abdominal cavity is usually accomplished by use of a system comprised of a cannula assembly and a trocar. A cannula assembly is formed of a cannula attached to a valve assembly which is adapted to maintain a seal across the opening of the valve assembly. Since the cannula is in direct communication with the internal portion of the valve assembly, insertion of the cannula into an opening in the patient's body so as to reach the inner abdominal cavity should be adapted to maintain a fluid tight interface between the abdominal cavity and the outside atmosphere.

Since surgical procedures in the abdominal cavity of the body require insufflating gases to raise the cavity wall away from vital organs, the procedure is usually initiated by use of a Verres needle through which a gas is introduced into the body cavity. Thereafter, a trocar, which is a sharp pointed instrument, is inserted into a cannula assembly and used to puncture the peritoneum, i.e. the inner lining of the abdominal cavity wall. The gas provides a slight pressure which raises the wall surface of the peritoneum away from the vital organs thereby avoiding unnecessary contact with the organs by the instruments inserted into the cannula. This procedure also provides the surgeon with an adequate region in which to operate. Laparoscopic or endoscopic surgical instruments may then be inserted through the cannula to perform surgery within the abdominal cavity or other body portion. The cannula is also utilized for introducing tubes into the body as for drainage purposes or the like.

In view of the need to maintain the atmospheric integrity of the inner area of the cavity, a valve assembly which permits introduction of a trocar or any surgical instrument and which permits selective communication of the inner atmosphere of the cavity with the outside atmosphere is desirable. In this regard, there have been a number of attempts in the prior art to provide such atmospheric integrity.

One form of cannula assembly includes a valve assembly which includes a flapper valve which is pivotally mounted within the valve assembly and is automatically opened by the trocar or other object when it is inserted into the proximal end of the valve assembly. See, e.g., U.S. Pat. No. 4,943,280 to Lander.

U.S. Pat. No. 4,960,412 relates to a catheter introducing system which includes a valve assembly having dual flexible resilient gaskets which permit introduction of a catheter by providing dual openings which are dimensioned to contact a catheter tube introduced into the unit. Introduction of the tube is accomplished by introducing the tube into the openings of the gaskets. A first valve prevents or minimizes the flow of blood from the valve assembly unit when the catheter tube is absent and the second valve prevents or minimizes the flow of blood from the valve assembly when the catheter tube is present.

Another valve includes finger operated levers for controlling an inner valve formed of a plurality of radially movable members which join in adjacent relation to close the valve opening and which separate to permit entry of an element into the valve opening. The members are concentrically positioned and arranged to block the opening when the levers are at rest and to open in a manner to form a substantially circular passage-way when the levers are squeezed toward each other against the bias of a spring positioned therebetween.

Although attempts have been somewhat successful in providing a valve assembly which maintains the integrity of the atmospheric interface between the inlet of the valve assembly and the atmosphere outside the valve assembly, none have provided the degree of control to the user whereby opening adapted to facilitate the introduction of an instrument into the human body can be controlled selectively, opened or closed, in sequence and in a manner which positively retains the desired interface between th two atmospheres as may be required by the operator. The present invention provides a valve assembly which may be incorporated into a cannula assembly or utilized in combination with any type of tubular member for introduction into the body of a patient while permitting introduction of instruments into the body. At all times, the surgeon maintains control over the interface between the atmospheres within and without the patient's body. Moreover, the present invention makes it possible to introduce instruments of varying sizes into the body and insures the maintenance of a gas seal despite instrument manipulation therethrough.

SUMMARY OF THE INVENTION

A valve assembly adapted for introduction of an elongated object into a patient's body is provided which comprises first valve means formed of a resilient material and defining an aperture for reception of the object, the aperture being configured and dimensioned such that insertion of the object into the aperture will cause the resilient material defining the aperture to resiliently engage the outer surface of the object in a substantially fluid tight manner. Second valve means is positioned adjacent the first valve means in general alignment therewith, the second valve means defining an aperture in general alignment with the aperture of the first valve means and being formed of a flexible material at least in the region defining the aperture. Means is provided to selectively permit the aperture of the second valve means to be opened or closed so as to permit entry of the object.

Preferably, the valve assembly comprises valve body means which defines proximal inlet and distal outlet openings. The first valve means is formed of an elastomeric resilient material and extends across the proximal inlet opening of the valve body, and defines an aperture configured and dimensioned for reception of the object in a manner such that resilient material surrounding the aperture engages the surface of the object to provide a substantially fluid tight seal which prevents passage of fluids past the interface. The second valve means is positioned adjacent and distally of the first valve means and both valve means extend across the proximal inlet opening of the valve body. The second valve means includes an aperture defined at least in part by flexible elastomeric material in general alignment with the aperture of the first valve means and of dimension sufficient to permit passage of the object after the object is passed through the first valve means. Means is provided to bias the flexible material defining the aperture of the second valve means to a configuration whereby the aperture is closed to form a fluid tight seal prior to inserting the object therethrough, and means is provided to open the aperture of the second valve means to permit passage of the object therethrough after the object is passed through the first valve means. Preferably, means to open the aperture of the second valve means is manually operable.

The objects contemplated are surgical instruments such as clip appliers, dissectors, graspers, laser and electrocautery devices, drainage or fluid introduction tubes or the like. The first valve means is positioned across the proximal opening of the valve body and the second valve means is positioned adjacent the first valve means and distally thereof. Further, the first and second valve means are preferably formed integrally of a flexible elastomeric resilient material, with the first valve means connected to the second valve means at the proximal ends thereof, the first valve means being positioned at least partially within the second valve means. The first and second valve means are joined at their proximal ends and are attached to the valve body across the proximal opening. The valve body includes a neck which extends distally of the distal end thereof, the neck defining an opening communicating with the interior of the valve body means. Further, the distally extending neck of the valve body is adapted to receive a tubular cannula such that the cannula extends distally of the valve body.

The second valve means comprises an elastomeric generally cylindrically shaped member which is preferably connected integrally at the proximal end thereof to the proximal end of the first valve means and is open at the distal end. The distal opening of the second valve means is capable of being closed by collapsing the distal end until the half portions thereof resiliently contact each other to form a substantial fluid tight seal. The distal end of the second valve means is biased toward the closed fluid tight position by a clamp which is positioned and adapted to bias the open end of the second valve means toward the collapsed configuration. The clamp comprises a pair of clamp blades, each blade connected to a portion of the distal open end of the second valve means. The clamp blades are each biased toward each other to close the distal opening of the second valve means by a respective torsion spring mounted within the valve body. Each clamp blade is connected to a pivotal arm and each pivotal arm is biased toward the position corresponding to the closed position of the second valve means. The pivotal arms are mounted for pivotal movement toward the valve-open position by reception into an aperture of at least one slidable pin. The pins are movable manually by engagement by the user's fingers.

The first and second valve means are preferably attached to and supported by an annular ring which includes a plurality of elongated fingers which extend distally therefrom and are positioned within the first valve means in contact with the inner surface thereof. The fingers provide an interface between the first valve means and objects inserted therein and assist in spreading the opening of the first valve means for entry of the instrument. Further, the fingers distribute the force over the inner surface of the first valve means.

Each slidable pin has a frusto-conical shaped tip adjacent each pivot arm for engagement with the respective pivot arm when the pins are moved toward each other by manual action of the user. Further, the valve body is preferably a two piece valve housing assembled at a medial interface and constructed of a relatively rigid plastic material such as polycarbonate, polyethylene or the like.

In a preferred embodiment, a cannula and trocar assembly is provided for puncturing a body wall of a patient for the introduction of elongated objects as surgical instruments or the like into the body of the patient while maintaining a substantial fluid tight seal between internal body portions and the outside atmosphere at all times prior to and after insertion of the object. The valve housing has an inlet opening at the proximal end and an outlet opening at the distal end, the distal end opening having a tubular cannula extending distally therefrom. A trocar is positioned within the valve housing and the cannula for puncturing the body wall. Thereafter, the trocar is removed and elongated objects such as surgical instruments or the like may be introduced into the patient's body through the valve assembly and cannula as described hereinabove.

In the preferred embodiment the first and second valves are molded integrally of synthetic or natural rubber and are connected at a common proximal end which defines the proximal opening. The first valve means has a generally conical shape and is positioned within the second valve means in a generally concentric fashion. The valve means are mounted onto a support ring which is used to mount the valve means to an annular portion within the valve housing.

A method is provided for selectively sealing a valve assembly for communication with inner portions of a patient's body while permitting introduction of an elongated instrument therethrough, the valve assembly having a proximal inlet opening and a distal outlet opening, comprising providing first valve means comprised of resilient material defining an opening which permits entry therethrough by the instrument while resiliently contacting the outer surface, providing second valve means distal of the first valve means, and selectively controlling the open and closed condition of the second valve means to permit passage of the instrument after entry through the first valve means.

DETAILED DESCRIPTION OF THE PREFERRED EMBODIMENTS

The present invention contemplates introduction into a patient's body of all types of surgical instruments including clip appliers, lasers, photographic devices, tubes, etc. All such objects are referred to herein as "instruments".

Figure 1:
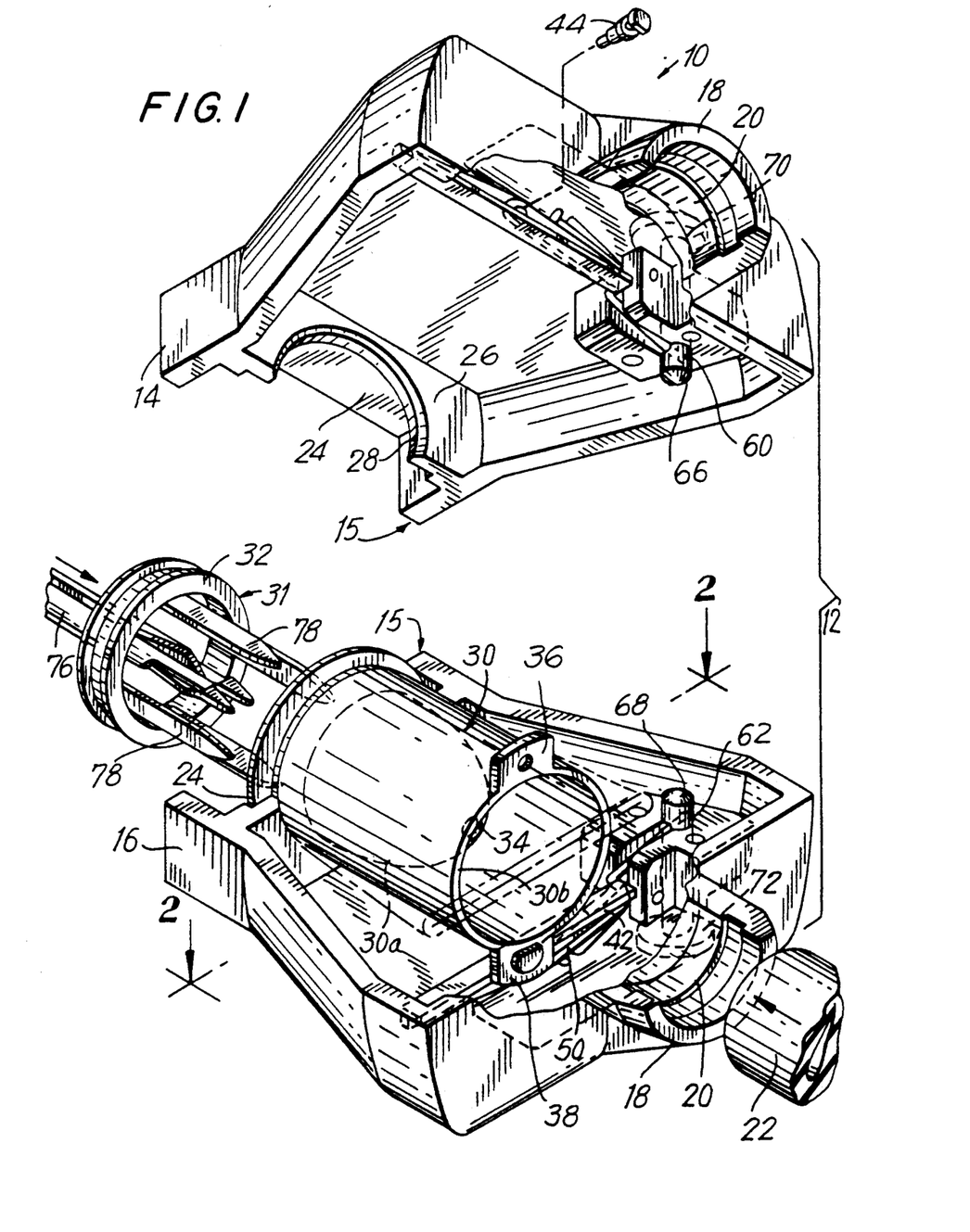
FIG. 1 is an exploded perspective view of a cannula assembly illustrating the valve assembly constructed according to the present invention.
Figure 2:
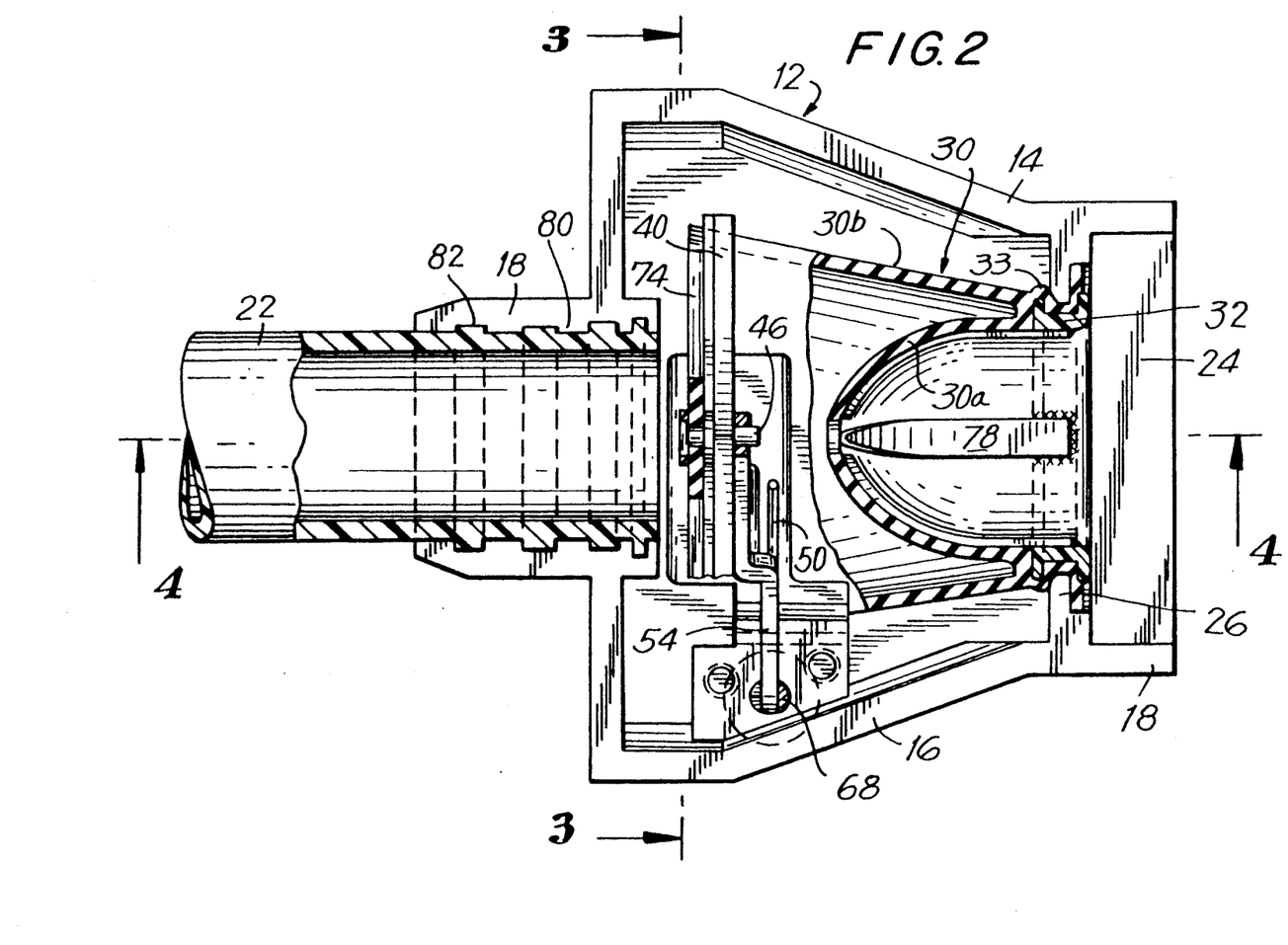
FIG. 2 is a view of the lower housing half section shown in FIG. 1 with portions of the inner valve and cannula cut away for illustration purposes.

Referring initially to FIGS. 1 and 2, a cannula assembly 10 is illustrated having the novel valve assembly 12 constructed according to the present invention. Valve assembly 12 includes a valve housing 15 formed of upper housing half section 14 and lower housing half section 16 shown separated in FIG. 1 for convenience of illustration.

The housing half sections 14,16 are formed of a suitable desirable plastic material such as polycarbonate, polyethylene or the like. One preferred material is LEXAN brand polycarbonate manufactured and marketed by General Electric Company, Pittsfield, Mass. The housing half sections 14,16 are normally attached along the seam by suitable attachment techniques such as adhesive, ultrasonic welding, or the like.

The valve housing 15 includes neck 18 at the distal end having an aperture 20 dimensioned for reception of an appropriate sheath tube such as cannula 22 to form the cannula assembly 10. The proximal end of valve housing 15 includes inlet opening 24 which includes annular partition 26 for supporting a dual diaphragm as will be described.

Referring now to FIG. 2, the lower housing half section 16 is shown with the upper housing half section 14 removed, so as to illustrate the novel inner valve mechanism of the present invention. The valve mechanism is shown partially cut away and in cross section. Dual flexible elastomeric sealing diaphragm 30 extends across the aperture 20 of housing 15 as shown. The diaphragm 30 forms a circular rib 33 which fits tightly by snap fit onto annular partition 26 with dual flanged circular rib 32 as shown in FIG. 2. The annular partition 26 is constructed of the same relatively rigid plastic material such as polycarbonate, polyethylene or the like, as the valve housing, while diaphragm 30 is constructed of an elastomeric material such as synthetic or natural rubber. Diaphragm 30 is of dual walled construction as shown, with the inner wall 30a having a central aperture 34 for reception of an instrument as will be described.

Figure 3:
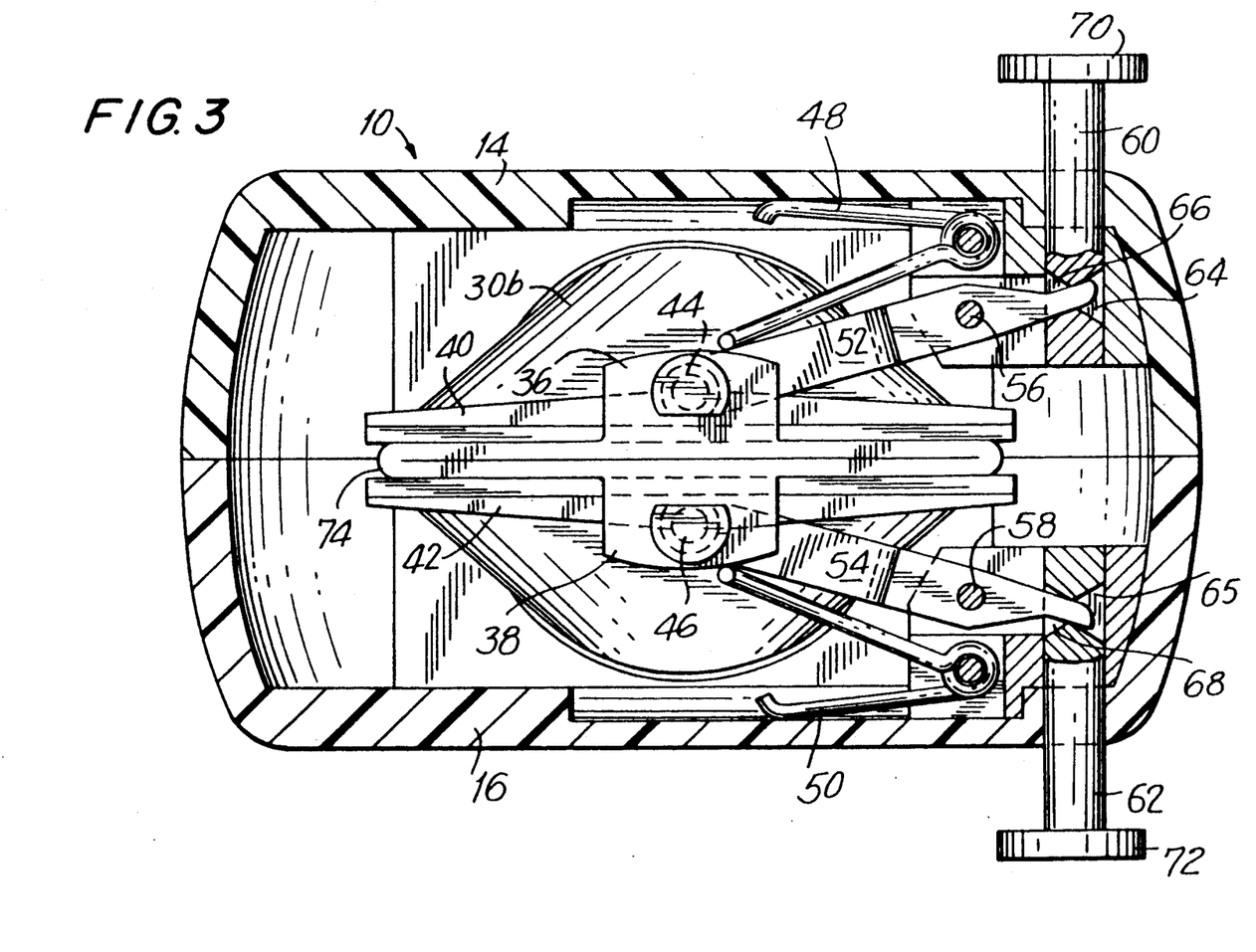
FIG. 3 is a cross-sectional view of the valve assembly of the present invention taken along lines 3—3 of FIG. 2.
Figure 4:
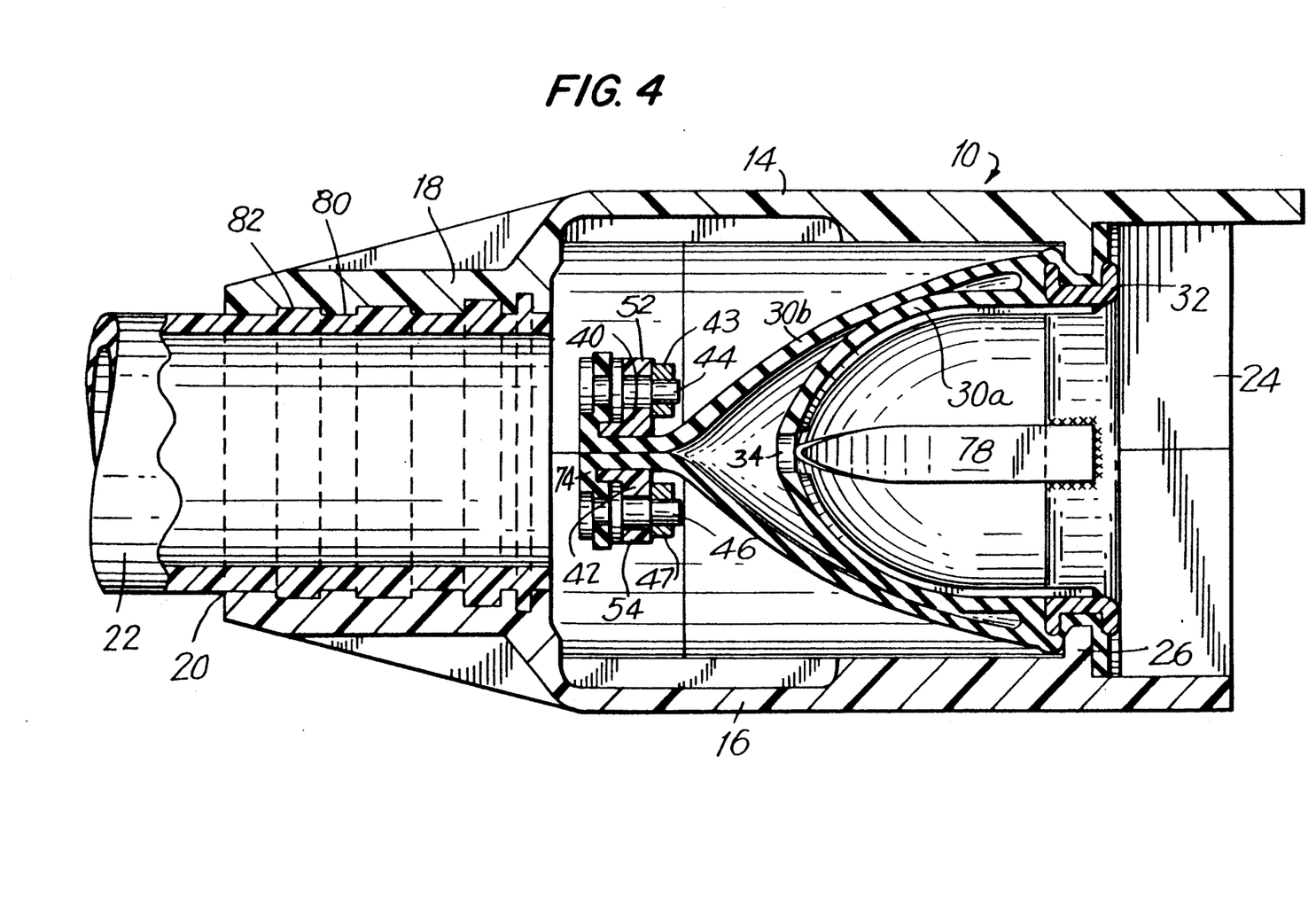
FIG. 4 is a cross-sectional view of the valve assembly of the present invention, taken along lines 4—4 of FIG. 2.

Referring now to FIG. 1 in conjunction with FIGS. 3 and 4, outer wall 30b has formed at the distal end, a pair of ears 36,38 which are connected to clamp blades 40,42 as shown, by suitable pivot pins 44,46 and attachment nuts 43,47. Each clamp blade 40,42 is biased in a direction toward the other by a torsion spring 48,50 having one leg in engagement with the adjacent housing wall and the other leg in engagement with pivotal arm 52,54 respectively pivotally mounted at pivot pin 56,58 as shown in FIG. 3. Each pivot arm 52,54 extends as shown, into the path of a pin 60,62 which is slidably mounted within elongated opening 64,65 having a circular cross-section similar to the cross-section of the pins 60,62. The inner end of each pin has an opening 66,68 for reception of the appropriate pivotal arm 52,54 such that manually depressing the slidable pins 60,62 toward each other by engagement of transverse buttons 70,72 with the thumb and index finger causes pivotal arms 52,54 to pivotally rotate arms 52,54 away from each other. This motion causes clamp blades 40,42 with ears 36,38 to separate causing outer wall 30b of dual diaphragm 30 to open at the distal end to the configuration shown in FIG. 1. When the pins 60,62 are released, the outer wall 30b of diaphragm 30 collapses to the configuration shown in FIGS. 3 and 4 under action of clamp blades 44,46 and springs 48,50, thus causing outer wall to collapse to the duckbill shape 74, providing a fluid tight seal between the proximal end of the diaphragm 30 and the distal end.

Referring now to FIG. 4 in conjunction with FIG. 1, inner elastomeric wall 30a of diaphragm 30 defines circular central aperture 34 at the distal end which is dimensioned less than or equal to the outer diameter of any instrument intended for entry into the proximal end of the valve assembly. Preferably, diaphragm 30 is fabricated from a material which is sufficiently resilient to accommodate and provide a fluid seal with instruments of varying diameters, e.g., diameters of from 5 mm to 10 mm. In FIG. 1 an endoscopic clip applying apparatus is shown at 76. However, any elongated relatively narrow instrument is contemplated.

Referring once again to FIG. 3 in conjunction with FIG. 1, diaphragm mounting and stabilizing device 31 is formed of dual flanged circular ribbed ring 32 having distally extending fingers 78 tapered at their free ends as shown. Diaphragm 30 is mounted to dual flanged circular ring 32 as shown in FIG. 4 and the entire assembly is mounted to annular partition 26 as shown. Fingers 78 are positioned within diaphragm inner wall 30a and are sufficiently flexible to conform to the shape of the inner wall while providing some degree of stability to the inner wall. Fingers 78 also assist in spreading inner wall 30a to expand aperture 34 when an instrument is inserted by distributing the spreading force more evenly. In addition to facilitating expansion of aperture 34 to conform to instrument 76, fingers 78 minimize the risk of damage to elastomeric inner wall 30a, e.g., puncture thereof, by providing an interface between the instrument 76 and the inner wall. Stabilizing device 31 is fabricated of a suitable flexible plastic material such as polyester, polypropylene, etc. and fingers 78 are preferably formed integral with dual flanged ring 32. Further, fingers 78 are sufficiently thin and flexible such that insertion into inner wall 30a of diaphragm 30 causes them to assume an initial arcuate shape as shown in FIGS. 2 and 4, similar to the generally conical shape of inner wall 30a.

Upon insertion of instrument 76 into housing opening 20 and through aperture 34 of inner wall 30a, the elastomeric material of wall 30a will expand or stretch around the instrument 76 to form a fluid tight seal. The seal is of sufficient fluid tight character that media such as pressurized gases used to insufflate a body cavity or body liquids will not pass the interface between diaphragm inner wall 30a and the instrument 76. Aperture 34, in its non-expanded or non-stretched condition, is typically approximately 3 to 15 mm to accommodate elongated endoscopic instruments while maintaining sufficient sealed contact with the other surface thereof. However, such dimensions will vary depending upon the size of the instruments and the intended application. Further, manipulation of the instrument in any direction will not affect the seal, since the elastomeric material will remain in tight contact with the outer surface of the instrument.

At the point when the instrument 76 has passed the inner wall 30a and entered aperture 34, a gas tight seal has been created between the instrument and the inner wall 30a. The surgeon then squeezes pins 60,62 with the thumb and index finger causing the distal end of outer wall 30b of diaphragm 30 to expand to the shape shown in FIG. 1 thus permitting continued entry of the instrument 76 through the entire valve body housing 15 and into the cannula 22. Depending upon the particular procedure, the surgeon may prefer to squeeze pins 60,62 thereby opening outer wall 30b prior to entry of instrument 76 into the valve housing 15 and into diaphragm inner wall 30a.

Cannula 22 is connected to the distal end of the valve housing at neck 18 which has a series of alternating circular shaped ribs 80 and valleys 82. Cannula 22 is fabricated of a rigid material such as a plastic, fiberglass or metal and is supported in position as shown in FIGS. 2 and 4 within neck 18 by the ribs 80 which are formed of the same material. Alternatively, the tube 22 may be of elastomeric material in which case it would simply be flexible and resilient so as to be assembled with distal neck 18 by inserting the tube into the neck and distorting the outer shape until it is snapped into position as shown within ribs 80.

The operation of the valve assembly will now be described. The valve assembly is intended to be supplied as part of a cannula assembly, i.e. a valve assembly with distal cannula tube 22 positioned as shown. A trocar is a sharp pointed instrument usually fitted within a cannula assembly and used to insert the cannula into a body cavity by first piercing an aperture in the cavity wall (i.e., the peritoneum). The cannula is then inserted into the punctured body wall of the patient. Thereafter, the trocar is removed, permitting insertion of instruments into the patient's body through the cannula to perform the desired procedure. Thus, the significance of providing control to the surgeon of the sealed state of the opening in the cannula assembly cannot be overemphasized. Such opening will ultimately control the exposure between the internal part of the body cavity and the outside atmosphere. For laparoscopic procedures the valve assembly will preserve the state of insufflation of the peritoneum during the surgical procedures.

The surgeon removes the trocar from the cannula assembly thereby permitting the opening of outer wall 30b of diaphragm 30 to close automatically under the action of springs 48,50. Thereafter, the surgeon inserts an instrument into the body cavity by first inserting it into the proximal end of the valve assembly, through dual flanged ring 32 and then through aperture 34 of inner diaphragm wall 30a. Pins 60,62 may be selectively squeezed as desired by the surgeon to open the distal end of outer wall 30b to permit entry of the instrument into cannula 22 and into the body cavity. At this point, the tight contact between the instrument 76 and the diaphragm inner wall 30a at aperture 34 has sealed the inner body cavity from the outside atmosphere. This seal is provided by the resilient property of the stretched elastomeric material surrounding opening 34. Thus, separating clamp plates 40,42 to open outer diaphragm wall 30b to permit entry of instrument 76 into cannula 22 does not affect the sealed condition of the inner anatomical cavity. As noted previously, manipulation of the instrument in any direction will not affect the seal, since the elastomeric material defining the opening 34 will conform to the movements of the instrument and assume an elliptical or other shape necessary to maintain contact.

As noted, aperture 34 is preferably dimensioned between 3 and 15 mm to accommodate laparoscopic and endoscopic instruments such as clip appliers, laser tubes, photographic instruments, tubes or the like. However, depending upon need or application this dimensional range may be varied to accommodate any particular instrument.

The opening at the distal end of outer wall 30b is always under the surgeon's control through pins 60,62 and is adapted to be automatically actuated to the closed duckbill shaped position 74 under action of springs 48,50 when the surgeon removes the instrument 76 or other object from the valve assembly. Further, manipulation of the instrument 76 does not affect the shape of aperture 34 or the sealing contact of inner wall 30 or with the instruments because diaphragm 30 is sufficiently flexible and resilient to maintain contact with the surface of the instrument 76. Thus, during the entire sequence the integrity of the seal between the inside of the body cavity and the outside atmosphere is clearly maintained at all times.

We claim:

1. A valve assembly adapted for introduction of an elongated object into a patient's body which comprises:
    (a) first valve means formed of a resilient material and defining an aperture for reception of the object, said aperture being configured and dimensioned such that insertion of the object into said aperture will cause the resilient material defining said aperture to resiliently engage the outer surface of the object in a substantially fluid tight manner;
    (b) second valve means positioned adjacent said first valve means in general alignment therewith, said second valve means defining an aperture in general alignment with said aperture of said first valve means, and being formed of a flexible material at least in the region defining said aperture; and
    (c) manually operable means to selectively permit said aperture of said second valve means to be opened or closed so as to permit entry of the object.

2. A valve assembly for introduction of a surgical instrument into a patient's body while selectively maintaining a fluid tight seal between the inner portion of the patient's body and the outside atmosphere, which comprises:
    (a) valve body means defining proximal inlet and distal outlet means;
    (b) first valve means formed of a resilient material and extending across said proximal inlet means of said valve body means, said first valve means defining an aperture configured and dimensioned for reception of the object, in a manner such that resilient material surrounding aperture engages the surface of the object to provide a substantially fluid tight seal which prevents passage of fluids past the interface;

(c) second valve means positioned adjacent and distally of said first valve means and extending across said proximal inlet means of said valve body means, said second valve means including an aperture defined at least in part by flexible material and in general alignment with said aperture of said first valve means and of dimension sufficient to permit passage of the object after the object is passed through said first valve means;

(d) means to bias said flexible material defining said aperture of said second valve means to a configuration whereby said aperture is closed to form a fluid tight seal prior to inserting the object therethrough; and (e) means to open said aperture of said second valve means to permit passage of the object therethrough when the object is passed through said first valve means.

3. The valve assembly according to claim 2 wherein said means to open said aperture of said second valve means is manually operable.

4. A valve assembly for introduction of elongated objects into a patient's body while maintaining the atmospheric integrity therein, which comprises:

(a) valve body means defining a proximal inlet opening and a distal outlet opening;

(b) first valve means formed of a flexible elastomeric resilient material and defining an aperture for reception of the object, said aperture being configured and dimensioned such that insertion of the object into said aperture will cause the flexible resilient material defining said aperture to resiliently engage and conform to the outer surface of the object in a substantially fluid tight manner;

(c) second valve means positioned adjacent said first valve means in general alignment therewith, said second valve means defining an aperture in general alignment with said aperture of said first valve means, and being formed of a flexible resilient material at least in the region adjacent to and defining said aperture; and (d) manually operable means to selectively open said aperture of said second valve means whereby the object may pass therethrough.

5. The valve assembly according to claim 4 wherein the object comprises a surgical instrument.

6. The valve assembly according to claim 5 wherein said first valve means is positioned across said proximal opening of said valve body means and said second valve means is positioned adjacent said first valve means and distally thereof.

7. The valve assembly according to claim 6 wherein said first and second valve means are formed integrally of a flexible elastomeric resilient material, said first valve means connected to said second valve means at the proximal end thereof, said first valve means being positioned at least partially within said second valve means.

8. The valve assembly according to claim 7 wherein said first and second valve means are joined at the proximal end and are attached to said valve body means across the proximal opening thereof.

9. The valve assembly according to claim 8 wherein said valve body means comprises a neck extending distally of the distal end thereof, said neck defining an opening communicating with the interior of said valve body means.

10. The valve assembly according to claim 9 wherein said distally extending neck of said valve body means is adapted to receive a tubular member such that said tubular member extends distally of said valve body means.

11. The valve assembly according to claim 10 wherein said second valve means comprises an elastomeric generally cylindrically shaped member connected integrally at the proximal end thereof to said proximal end of said first valve means and being open at the distal end, said distal opening being capable of being closed by collapsing said distal end of said second valve means until the half portions thereof resiliently contact each other to a duckbill shape to form a substantial fluid tight seal.

12. The valve assembly according to claim 11 wherein said open distal end of said second valve means is biased toward the closed fluid tight position.

13. The valve assembly according to claim 12 wherein clamp means is positioned and adapted to bias said open end of said second valve means toward the collapsed configuration.

14. The valve assembly according to claim 13 wherein said clamp means comprises a pair of clamp blades, each blade connected to a portion of said distal open end of said second valve means, said clamp blades being biased toward each other to close the distal opening of said second valve means.

15. The valve assembly according to claim 14 wherein said clamp blades are each biased toward the other by a respective torsion spring mounted within said valve body.

16. The valve assembly according to claim 15 wherein each said clamp blade is connected to a pivotal arm and each pivotal arm is biased toward the position corresponding to the closed position of said second valve means.

17. The valve assembly according to claim 16 wherein each said pivotal arms is mounted for pivotal movement toward the valve-open position by engagement with at least one slidable pin.

18. The valve assembly according to claim 17 wherein each said pin is positioned for slidable movement within said valve body means and is movable manually by engagement by the user's fingers, each said pin defining an opening for reception of the free end portion of the respective pivot arm.

19. The valve assembly according to claim 18 wherein said proximal end of said first and second valve means is attached to and supported by an annular ring.

20. The valve assembly according to claim 19 wherein said annular ring includes a plurality of elongated fingers which extend distally therefrom and are positioned within said first valve means in supporting contact with the inner surface thereof, said fingers providing an interface between said first valve means and objects inserted therein.

21. The valve assembly according to claim 20 wherein each said slidable pin has a frusto-conical shaped tip adjacent each pivot arm for engagement with said respective pivot arm when said pins are moved toward each other by manual action of the user.

22. The valve assembly according to claim 21 wherein said valve body means is a two piece valve housing assembled at a medial interface.

23. The valve assembly according to claim 22 wherein said valve housing is constructed of a relatively rigid plastic material such as polycarbonate, polyethylene or the like.

24. A valve assembly for introduction of an elongated object such as a surgical instrument or the like into the body of a patient while maintaining substantial fluid tight seal between internal body portions and the outside atmosphere at all times prior to and after insertion of the object, which comprises:
- (a) a valve housing having an inlet opening at the proximal end and an outlet opening at the distal end;
- (b) first valve means formed of a resilient material and extending across said inlet opening of said valve housing, said first valve means defining an aperture dimensioned for reception of the object in a manner such that resilient material surrounding said aperture engages the surface of the object in conforming relation therewith to provide a substantial fluid tight seal which prevents passage of fluids past the interface;
- (c) second valve means formed of a resilient material and positioned adjacent said first valve means and extending across the inlet opening of said valve housing, said second valve means defining an aperture in general alignment with said aperture of said valve means and distally thereof, said distal aperture being of dimension sufficient to permit passage of the object after the object is passed through said aperture of said first valve means;
- (d) a pair of plate members positioned to engage the portion of said second valve means defining said distal aperture, said plate members being biased toward each other by resilient spring means to bias the resilient material surrounding said distal aperture of said second valve means to a configuration whereby said aperture is closed to form a fluid tight seal prior to positioning the object therein; and
- (e) manually operable means adapted to separate said plate members in a manner to open said aperture of said second valve means to permit passage of the object therethrough when the object is passed through said first valve means.

25. The valve assembly according to claim 24 wherein said first and second valve means are integrally formed of an elastomeric material.

26. The valve assembly according to claim 25 wherein said first valve means is positioned within said second valve means and said first and second valve means are connected to each other at the proximal ends thereof, said first and second valve means each defining an opening at the distal ends thereof 27. The valve assembly according to claim 26 wherein said first valve means has a generally conical configuration.

28. The valve assembly according to claim 26 wherein said first and second valve means are supported on valve support means which comprises a support ring defining mounting flange means, said support ring having a plurality of distally extending resilient flexible fingers positioned within said first valve means to provide support to said first valve means such that when objects are inserted into said distal opening of said first valve means, said fingers provide an interface between said first valve means and the object to prevent damage to said first valve means prior to insertion of the object into said distal aperture of said first valve means.

29. The valve assembly according to claim 28 wherein said first and second valve means are integrally molded of synthetic or natural rubber.

30. A cannula and trocar assembly for puncturing a patient's body wall for the introduction of elongated objects such as surgical instruments or the like into the body of a patient while maintaining a substantial fluid tight seal between internal body portions and the outside atmosphere at all times prior to and after insertion of the object, which comprises:
- (a) a valve housing having an inlet opening at the proximal end and an outlet opening at the distal end, said distal end opening having a tubular cannula extending distally therefrom;
- (b) a trocar positioned within said valve housing and said cannula;
- (c) first valve means formed of a resilient material and extending across the inlet opening of said valve housing, said first valve means defining an aperture dimensioned for reception of said trocar or the object in a manner such that resilient material surrounding said aperture engages the surface of the trocar or the object to provide a substantial fluid tight seal which prevents passage of fluids past the interface;
- (d) second valve means of resilient material positioned distal and adjacent said first valve means and extending across the inlet opening of said valve housing, said second valve means defining an outlet aperture in general alignment with said distal aperture of said valve means and of dimension sufficient to permit passage of the trocar or object after the trocar or object is passed through said first valve means;
- (e) a pair of plate members positioned within said valve housing to engage the portion of said second valve means defining said aperture, said plate members biased toward each other by resilient spring means to bias the resilient material surrounding said aperture of said second valve means to a configuration whereby said aperture is closed to form a fluid tight seal prior to positioning the object therein; and
- (f) manually operable means adapted to separate said plate members in a manner to open said aperture of said second valve means to permit passage of the object therethrough when the object is passed through said first valve means.

31. The valve assembly according to claim 30 wherein said first and second valve means are integrally molded of synthetic or natural rubber, said first and second valve means being connected at the proximal end and defining a proximal opening, said first valve means having a generally conical shape and being positioned within said second valve means, said second valve means having a generally cylindrical shape when said distal outlet aperture is opened and being collapsible at the outlet end in a manner to provide contact between the two half portions to provide a substantial fluid tight seal.

32. A method of selectively sealing a valve assembly for communication with inner portions of a patient's body while permitting introduction of an elongated instrument therethrough, said valve assembly having a proximal inlet opening and a distal outlet opening, comprising:
- (a) providing first valve means comprised of resilient material defining an opening which permits entry therethrough by the instrument while resiliently contacting the outer surface;
(b) providing second valve means distal of said first valve means; and
(c) selectively controlling the open and closed condition of said second valve means to permit passage of said instrument after entry through said first valve means.

* * * * *